United States Patent [19]

Hupe

[11] Patent Number: 5,045,543
[45] Date of Patent: Sep. 3, 1991

[54] 5-AMINO OR SUBSTITUTED AMINO 1,2,3-TRIAZOLES USEFUL AS ANTIMETASTATIC AGENTS

[75] Inventor: Donald Hupe, Westfield, N.J.

[73] Assignee: Merck & Co., Inc., Rahway, N.J.

[21] Appl. No.: 348,823

[22] Filed: May 8, 1989

Related U.S. Application Data

[63] Continuation-in-part of Ser. No. 87,494, Aug. 20, 1987, Pat. No. 4,847,257.

[51] Int. Cl.$^5$ .............................................. A61K 31/41
[52] U.S. Cl. .................................................... 514/359
[58] Field of Search ......................................... 514/359

[56] References Cited

U.S. PATENT DOCUMENTS 4,590,201  5/1986  Bochis et al. ...................... 514/359

FOREIGN PATENT DOCUMENTS 0151529  8/1985  European Pat. Off. .

OTHER PUBLICATIONS

Lucacchini et al., Ital. J. Biochem., vol. 28, No. 3, 194–206; 1979.
Kohn and Liotta, J. Nat. Cancer 82, 54–60, 1990.
American Heritage Dictionary, vol. 2, p. 286 (1982).
Berridge, M. J. Oncogenes, Inositol Lipis and Cellular Proliferatin, Biotechnology, pp. 541–546, (Jun. 1984).
Berridte, M. J., The Mollecular Basis of Communication within the Cell, vol. 254, pp. 142–152 (1985).
Bosma, A. and Sidell, N., Retinoic Acid Inhibits $Ca^{2+}$ Currents and Cell Proliferation in a B-Lymphocyte Cell Line, J. Cell. Phys., vol. 135 (88), pp. 217–232.
Carafoli, Eve and Penniston, J. T., Calcium Signal, Scientific American, vol. 63, pp. 70–78 (1985).
Current Therapy, pp. 738–742 (1981).
Kohn, E. C. et al., L 651582, A Novel Antiproliferative and Anti-Metastasis Agent Which Interferes with Guanine Nucleotide-Binding Protein.
Nardone, P. A. et al., Ketoconazole: A Thromboxane Synthetase and 5-Lipoxygenase Inhibitor with Antimetastatic., Jour. Surg. Res. 44, pp. 425–429 (1988).

*Primary Examiner*—Jerome D. Goldberg
*Attorney, Agent, or Firm*—Curtis C. Panzer; Hesna J. Pfeiffer

[57] ABSTRACT

This invention is directed to the method of treating patients with surgically excised tumors with a high probability of metastasis, such as melanoma and breast cancer, by administering to such patient a nontoxic therapeutically effective amount of a 5-amino or substituted amino, 1,2,3-triazoles which are disclosed as a new class of antimetastatic agents useful in such treatment.

8 Claims, No Drawings

5-AMINO OR SUBSTITUTED AMINO 1,2,3-TRIAZOLES USEFUL AS ANTIMETASTATIC AGENTS

This application is a continuation-in-part of U.S. patent application Ser. No. 087,494, filed Aug. 20, 1987, now U.S. Pat. No. 4,847,257 issued July 11, 1989.

BACKGROUND OF THE INVENTION

5-Amino or substituted amino 1,2,3-triazoles have been known as anticoccidiosis agents. As such the compounds and the preparations thereof were disclosed in the U.S. Pat. No. 4,590,201. These compounds have also been described and disclosed as useful in the treatment of psoriasis in copending U.S. patent application Ser. No. 087,494, filed Aug. 20, 1987, now U.S. Pat. No. 4,847,257 issued July 11, 1989.

Psoriasis is a chronic skin disease which is characterized by hyperproliferation of the epidermis as well as by focal accumulations of lymphocytic cells. Cell cycle estimates in psoriasis suggest that the average germinative psoriatic cell divides every 37 hours compared to 152 hours in normal skin, and the role of hyperproliferation in the production of lesions is evidenced by the fact that antiproliferitive agents such as methotrexate are presently used therapeutically for symptomatic treatment of the disease. Other chemotherapeutic agents which have been used experimentally with success in clearing lesions include similar antimetabolites which disrupt nucleotide metabolism and thereby inhibit proliferation such as mycophenolic acid or thioguanine. The importance of the inflammatory component of the disease and the involvement of the arachidonate cascade in psoriasis is suggested by the elevated levels of arachidonate metabolites found in psoriatic skin compared to normal skin. Some of these metabolites, such as $LTB_4$ or 12-HETE, are potent chemoattractants capable of causing polymorphonuclear leukocyte invasion of the skin, whereas others such as prostaglandins $D_2$, $E_2$ and $I_2$ cause erythema, vasodilation and edema. The ability of glucocorticoids to inhibit the release of arachidonate by regulating phospholipase A2 is presumably responsible for at least part of the therapeutic value of this class of antipsoriatic agents.

In our in vitro studies on antiproliferative agents, it became apparent that 5-amino-1,2,3-triazoles were topically active antiproliferative agents which also inhibited the production of a broad array of arachidonate metabolites. Therefore, it appeared that these compounds would be able to simultaneously inhibit both of the pathological states associated with the psoriasis. Rather than being the fortuitous appearance of two unrelated pharmacological activities, the compound apparently inhibits the primary agonist-generated signal responsible for either the production of eicosanoids or for the initiation of cell division.

Upon further testing by accepted in vivo models, we were able to demonstrate that these amino-1,2,3-triazole analogs were potentially effective in the treatment and management of psoriasis, inflammatory bowel syndrome, cutaneous leishmanilisis, and might also be effective in the treatment of certain types of cancer that involved the transportation of individual cells to other tissues from a metastasizing tumor.

BRIEF DESCRIPTION OF THE INVENTION

The instant invention is directed to the treatment and management of certain types of cancer, which cancer involves the transportation of individual cells to other tissues from a metastasizing tumor, and which cancer is susceptible to treatment with specific amino-1,2,3-triazole analogs, said treatment utilizing the specific amino-1,2,3-triazole analogs.

DETAILED DESCRIPTION OF THE INVENTION

This invention relates to a method of treating cancer susceptible to treatment with a compound of formula (I), in a patient with surgically excised cancer tumors with a high probability of metastasis, such as melanoma and breast cancer, comprising:

administration to such a patient in need of such treatment, a nontoxic therapeutically effective amount of a compound of the following structural formula (I):

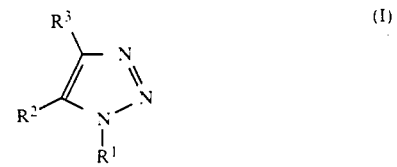

wherein:

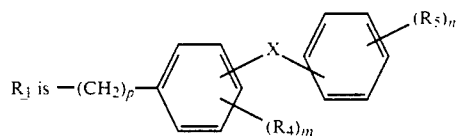

wherein p is 0 to 2; m is 0 to 4; and n is 0 to 5; X is O, S, SO, $SO_2$, CO, CHCN, $CH_2$ or $C=NR_6$ where $R_6$ is hydrogen, loweralkyl, hydroxy, loweralkoxy, amino loweralkylamino, diloweralkylamino or cyano; and, $R_4$ and $R_5$ are independently halogen, cyano, trifluoromethyl, loweralkanoyl, nitro, loweralkyl, loweralkoxy, carboxy, carbalkoxy, trifluoromethoxy, acetamido, loweralkylthio, loweralkylsulfonyl, loweralkylsulfonyl, trichlorovinyl, trifluoromethylthio, trifluoromethylsulfinyl, or trifluoromethylsulfonyl;

$R_2$ is amino, mono or diloweralkyl amino, acetamido, acetimido, ureido, formamido, formimido or guanidino; and $R_3$ is carbamoyl, cyano, carbazoyl, amidino or N-hydroxycarbamoyl.

One embodiment of this invention is the method in which the compounds of formula (I) wherein:

p is 1; X is O, S, CO or $CH_2$;

$R_4$ is fluoro, chloro, bromo, methyl, trifluoromethyl, cyano, carbomethoxy, trifluoromethoxy, trifluoromethylthio, or trichlorovinyl;

$R_5$ is halogen, methyl, trifluoromethyl, cyano, carbalkoxy, or trichlorovinyl;

$R_2$ is amino;

$R_3$ is carbamoyl ($-CONH_2$); and m and n independently are 0, 1 or 2 are utilized.

One class of this embodiment involves the use of the compounds of the formula (II)

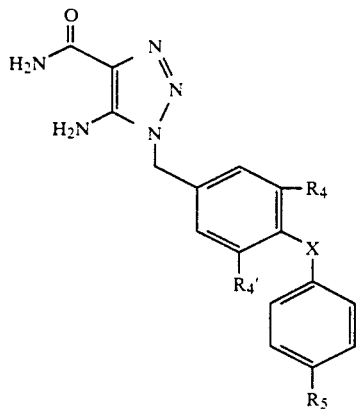

wherein
X is $CH_2$, S, O or (CO)—;
$R_4$ is Cl, $CF_3$, Br, or $CH_3$;
$R_4'$ is H or Cl; and $R_5$ is Cl, Br or $NO_2$.

This invention also relates to a method of treatment of a cancer susceptible to treatment with a compound of formula (I), said cancer involving the transportation of individual cells to other tissues from a metastasizing tumor comprising:

administration to a patient in need of such treatment an anti-proliferative, anti-metastatic effective amount of composition containing as its active ingredient the compound of the formula (I).

Specifically exemplifying the claimed invention is a method of treating a cancer susceptible to treatment with a compound which is 5-amino-1-(4-[4-chlorobenzoyl]-3,5-dichlorobenzyl)-1,2,3-triazole-4-carboxamide, said cancer in a patient with a surgically excised cancer tumor with a high probability of metastasis, such as melanoma and breast cancer comprising:

administration to a patient in need of such treatment a nontoxic therapeutically effective amount of compound which is 5-amino-1-(4-[4-chlorobenzoyl]-3,5-dichlorobenzyl)-1,2,3-triazole-4-carboxamide.

Further exemplifying the claimed invention is a method of treatment of a cancer susceptible to treatment with a compound which is 5-amino-1-(4-[4-chlorobenzoyl]-3,5-dichlorobenzyl)-1,2,3-triazole-4-carboxamide, said cancer involving the transportation of individual cells to other tissues from a metastasizing tumor comprising:

administration to a patient in need of such treatment an anti-proliferative, anti-metastatic effective amount of composition containing as its active ingredient the compound which is 5-amino-1-(4-[4-chlorobenzoyl]-3,5-dichlorobenzyl)-1,2,3-triazole-4-carboxamide.

The compounds to be used in this invention can be prepared by the procedures described in the U.S. Pat. No. 4,590,201 which is hereby incorporated by reference.

The compounds may also be prepared by the improved methods outlined below in Scheme I.

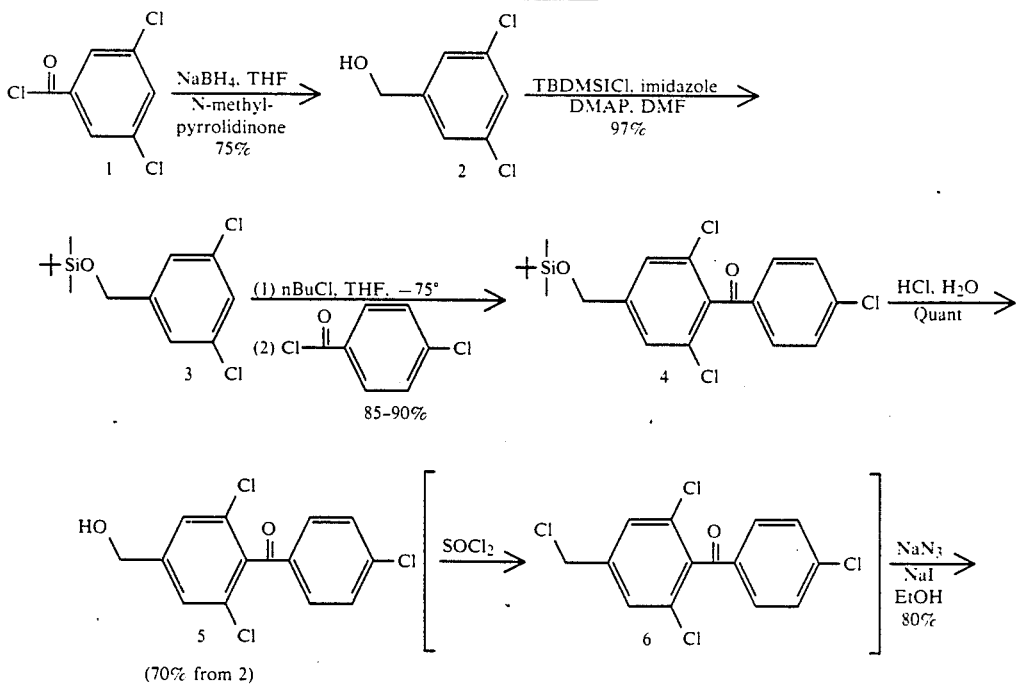

-continued
SCHEME 1

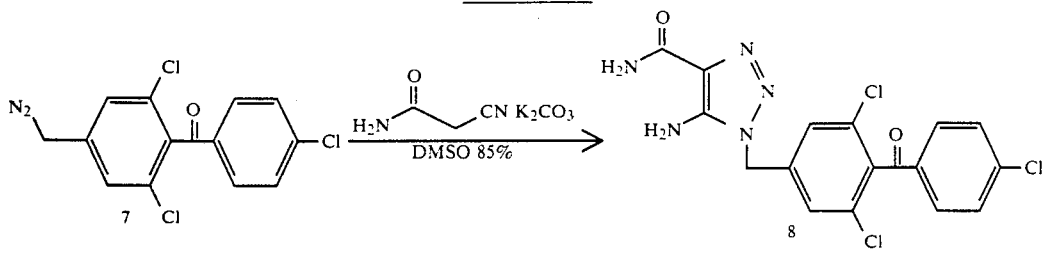

For the treatment of patients with surgically excised tumors with a high probability of metastasis, such as melanoma and breast cancer, a compound of formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets containing the active ingredient in admixture with non-toxic pharmaceutically acceptable excipients may also be manufactured by known methods. The excipients used may be for example, (1) inert diluents such as calcium carbonate, lactose, calcium phosphate or sodium phosphate; (2) granulating and disintegrating agents such as corn starch, or alginic acid; (3) binding agents such as starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874 to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example peanut oil, liquid paraffin, or olive oil.

Aqueous suspensions normally contain the active materials in admixture with excipients suitable for the manufacture of aqueous suspensions. Such excipients may be (1) suspending agents such as sodium carboxymethylcellulose, methylcellulose, hydroxypropylmethylcellulose, sodium alginate, polyvinylpyrrolidone, gum tragacanth and gum acacia; (2) dispersing or wetting agents which may be (a) a naturally-occurring phosphatide such as lecithin, (b) a condensation product of an alkylene oxide with a fatty acid, for example, polyoxyethylene stearate, (c) a condensation product of ethylene oxide with a long chain aliphatic alcohol, for example, heptadecaethyleneoxycetanol, (d) a condensation product of ethylene oxide with a partial ester derived from a fatty acid and a hexitol such as polyoxyethylene sorbitol monooleate, or (e) a condensation product of ethylene oxide with a partial ester derived from a fatty acid and a hexitol anhydride, for example polyoxyethylene sorbitan monooleate.

The aqueous suspensions may also contain one or more preservatives, for example, ethyl or n-propyl p-hydroxybenzoate; one or more coloring agents; one or more flavoring agents; and one or more sweetening agents such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an antioxidant such as ascorbic acid.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example, those sweetening, flavoring and coloring agents described above may also be present.

The pharmaceutical compositions of the invention may also be in the form of oil-in-water emulsions. The oily phase may be a vegetable oil such as olive oil or arachis oils, or a mineral oil such as liquid paraffin or a mixture thereof. Suitable emulsifying agents may be (1) naturally-occurring gums such as gum acacia and gum tragacanth, (2) naturally-occurring phosphatides such as soy bean and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

A compound of (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the active compounds are employed.

Dosage levels of the order from about 0.5 mg to about 100 mg per kilogram of body weight per day are useful in the treatment of the above-indicated conditions (from about 25 mg to about 5 gms. per patient per day).

The amount of active ingredient that may be combined with the carrier materials to produce a single dosage form will vary depending upon the host treated and the particular mode of administration. For example, a formulation intended for the oral administration of humans may contain from 5 mg to 5 gm of active agent compounded with an appropriate and convenient amount of carrier material which may vary from about 5 to about 95 percent of the total composition. Dosage unit forms will generally contain between from about 25 mg to about 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The compounds of the formula (I) exhibit inhibitory activity with regard to metastatis. Such activity may be due to direct inhibition of proliferation of single metastatic cells dosed with the active agent during transport in the plasma, inhibition of macrophage lysosomal content dumping which may play a role in the metastatic invation through basement membrane, or inhibition of metastatic cell migration induced by tumor autocrine factor.

A representative member of the compounds of formula (I), 5-amino-1-(4-[4-chlorobenzoyl]-3,5-dichlorobenzyl)-1,2,3-triazole-4-carboxamide, has exhibited such antimetastatic activity in the following standard in vitro protocol:

Black Charles River female mice (C57BL-6j) were injected in the flank muscle on day 1 with a cell suspension obtained from mincing PMT-6 fibroscaroma tumors. This highly metastatic tumor produces a large number of metastases in the lung during development of the primary tumor, so that the efficacy of potential antimetastatic agents can be contrasted with their ability to inhibit primary tumor growth in the same model. The mice were in 4 groups of 6 and were dosed daily with a 0.5% methylcellulose suspension of 5-amino-1-(4-[4-chlorobenzoyl]-3,5-dichlorobenzyl)-1,2,3-triazole-4-carboxamide, the active agent, given by gavage. Fresh drug suspensions were prepared daily. The doses, in 250 $\mu$L, were 0, 100, 250, and 500 mg/kg.

The average weights of the primary tumors retrieved from mice who survived longer than 17 days were: Control 6.0 g. (3.1–8.4 g); 100 mg/kg, 2.9 g. (2.1–5.6 g.); 250 mg/kg, 3.0 g (1.3–4.6 g.); and 500 mg/kg, 3.3 g. (2.0–6.5 g.). Therefore, there may be a small effect of the drug on the primary tumor.

The lungs of the mice were sectioned at intervals throughout the entire lung after fixing in 10% formalin, and the sections stained with H&E. The metastases found ranged from micrometases of just a few cells to enormous ones that could be easily seen without a microscope. Table A gives a gross count of the number of metastases in each of 3 size groups and demonstrates that there are a large drop in the number of metastases at even the lowest dose.

TABLE A

| Size Range | ORAL DOSE (mg/kg/d) | | | |
| --- | --- | --- | --- | --- |
| | Control | 100 | 250 | 500 |
| | Number of Metastases | | | |
| >0.01 mm | 3 | 0 | 0 | 1 |
| 0.01–0.1 mm | 24 | 0 | 3 | 3 |
| <0.01 mm | 102 | 6 | 9 | 6 |

It has been found that the compounds of formula (I) have antiproliferative activities. It has been demonstrated that specific inhibitors of nucleotide biosynthesis can control psoriasis, tumor formation and other proliferative disorders. For example, Mycophenolic acid, a specific inhibitor of guanine nucleotide production, controls psoriasis by causing remission when given orally, albeit with unacceptable side effects. Other specific inhibitors of purine or pyrimidine nucleotide biosynthesis, including methotrexate, fluorouracil, thioguanine and N-phosphonacetyl-L-aspartate have been shown to be effective in treating the disease, although each has unacceptable side effects due to toxicity. It is apparent, however, that those drugs that regulate the rate of proliferation of cells by inhibiting nucleotide biosynthesis should also demonstrate efficacy in psoriasis and other proliferative disorders.

In vitro experiments were carried out which demonstrated the efficacy of amino-1,2,3-triazoles, for example, 5-amino-1-(4-(4-chlorobenzoyl)-3,5-dichlorobenzyl)-1,2,3-triazole-4-carboxamide (Compound A) at 1 $\mu$g/ml in inhibiting nucleotide biosynthesis in a variety of mammalian cells in monolayer culture. Hypoxanthine, adenine and formate incorporation into nucleotide pools was disrupted which suggested that the biosynthesis of phosphoribosyl pyrophosphate, PRPP, was inhibited. PRPP synthetase activity was dramatically lowered by the drug in cell based experiments even though in vitro studies showed that no direct inhibition of the enzyme occurred. This novel means of inhibiting nucleotide biosynthesis suggested that the compound would be antiproliferative at the same concentrations, and this was demonstrated in a number of cell types including the Normal Human Epidermal Keratinocytes that are relevant for psoriasis. Compound A was shown to be the most valuable of a large number of analogs for psoriasis on the basis of efficacy in inhibition of proliferation in vitro, lack of toxicity or genotoxicity and metabolic stability in vivo, although there were a few analogs with greater activity in the antiproliferative assay.

Compound A was shown to inhibit $LTB_4$, 5-HETE, and HHT production in rat PMN's, as well as $LTC_4$ and $PGE_2$ production and lysosomal enzyme release in macrophages at the same 1 μg/ml levels that were effective against proliferation and nucleotide production. As in the case of nucleotide inhibition, no evidence of direct inhibition of the relevant enzymes such as 5-lipoxygenase or $LTA_4$ hydrolase was obtained and the drug effect appeared to be acting upon a regulatory system.

In vivo activities demonstrated for Compound A include activity against P388 leukemia in nude mice in a life prolongation assay at 60 mg/kg/d and higher doses. Topical activity against keratinocyte proliferation has been demonstrated by assessing the proliferation rate. A 2% formulation in Gel #1 (a combination of isopropyl myristate:crodamol:ethanol 1:1:2) applied topically inhibits completely the uv induced hyperproliferation in pig skin which is architecturally similar to human skin. The topical antiproliferative activities, along with in vitro antiproliferative activities against human keratinocytes and fibroblasts, provide the biological data in support of the claimed utility:

INHIBITION OF NUCLEOTIDE METABOLISM IN MAMMALIAN CELLS

Compound A and analogs are capable of inhibiting nucleotide biosynthesis in a variety of mammalian cell types. As shown in Table 1, 3H-hypoxanthine incorporation into Maden Darby Bovine Kidney (MDBK) cells is substantially reduced by incubating the cells with 1.0 μg/ml of Compound A in Eagles Minimal Essential media.

TABLE 1

| | 3H-Hypoxanthine Uptake | | | |
|---|---|---|---|---|
| Sample | Conc. (μg/ml) | Time (min.) | $DPM^a$ | % Inhibition |
| Control | — | 10 | 87000 | — |
| | | 20 | 140000 | — |
| | | 30 | 190000 | — |
| Compound A | 1.0 | 10 | 36000 | 59 |
| | | 20 | 40000 | 71 |
| | | 30 | 40000 | 79 |

$^a$DPM = decompositions per minute

Confluent cells were incubated in Eagles Minimal Essential media for 2.5 hours, then incubated with Phosphate buffered saline +Ca +Mg for 30 minutes, and then they were incubated with or without 1 μg/ml Compound A for 15 minutes. Media containing 100 μM 8-$^3$H-hypoxanthine with or without drug was incubated for the time shown with the cells after which they were quenched by immersion in ice cold buffer. The DPM measurements were made on aliquots of neutralized perchloric acid supernatants.

Inhibition data comparable to that in Table 1 were obtained when measuring the ability of the drug to inhibit the incorporation of either formate or adenine into soluble nucleotide pools.

INHIBITION OF PROLIFERATION OF MAMMALIAN CELLS IN CULTURE

The inhibition of PRPP biosynthesis by Compound A and analogs supported the claimed use of the compounds as antiproliferative agents, since this inhibition should prevent all de novo and salvage biosynthesis of purine and pyrimidine nucleotides. As shown in Tables 2-4, levels of approximately 1.0 μg/ml show substantial inhibition of growth of Normal Human Epidermal Keratinocytes (NHEK), Maden Darby Bovine Kidney cells or Normal Human Fibroblasts. The data from NHEK's is particularly important since it is the overproliferation of these cells that occurs in psoriasis.

TABLE 2

| Inhibition of NHEK's Growth by Compound A | | | |
|---|---|---|---|
| Conc. (μg/ml) | Time (day) | ABS-background (650 nm) | % Inhibition |
| 0 (Control) | 4 | .090 | — |
| | 5 | .190 | — |
| | 7 | .390 | — |
| 0.5 | 4 | .085 | 6 |
| | 5 | .115 | 40 |
| | 7 | .190 | 51 |
| 1.0 | 4 | .040 | 56 |
| | 5 | .050 | 74 |
| | 7 | .120 | 70 |
| 2.0 | 4 | .005 | 94 |
| | 5 | .010 | 95 |
| | 7 | .050 | 87 |

TABLE 3

| Inhibition of Fibroblast Growth by Compound A | | | |
|---|---|---|---|
| Conc. (μg/ml) | Time (days) | No. of Cells − seeding cells | % Inhibition |
| 0 (Control) | 2 | 10.5 × 10$^3$ | — |
| | 3 | 14 × 10$^3$ | — |
| | 6 | 23 × 10$^3$ | — |
| 0.1 | 2 | 4 × 10$^3$ | 62 |
| | 3 | 5 × 10$^3$ | 64 |
| | 6 | 19 × 10$^3$ | 18 |
| 0.2 | 2 | 5 × 10$^3$ | 48 |
| | 3 | 2 × 10$^3$ | 86 |
| | 6 | 16.5 × 10$^3$ | 28 |
| 0.4 | 2 | 7 × 10$^3$ | 33 |
| | 3 | 6.5 × 10$^3$ | 54 |
| | 6 | 13 × 10$^3$ | 44 |
| 1.0 | 2 | 2 × 10$^3$ | 81 |
| | 3 | 0 | 100 |
| | 6 | 6 × 10$^3$ | 74 |
| 2.0 | 2 | 2 × 10$^3$ | 81 |
| | 3 | .5 × 10$^3$ | 96 |
| | 6 | 4 × 10$^3$ | 83 |

TABLE 4

| Inhibition of the Growth of MDBK Cells by Compound A | | | |
|---|---|---|---|
| Conc. (μg/ml) | Time (days) | # Cells × 10$^6$ − # Cells Seeded | % Inhibition |
| 0 (Control) | 1 | 1.40 | — |
| | 3 | 4.86 | — |
| 1.0 | 1 | 0 | 100% |
| | 3 | 3.12 | 36% |
| 2.0 | 1 | 0 | 100% |
| | 3 | 0 | 100% |

A number of compounds have activity comparable to Compound A (Table 5). In these experiments Murine keratinocyte transformed cell line PAPp26 was cultured in Dulbecco's modified Eagle's medium with 10% fetal calf serum at 37° C., 5% $CO_2$. Each well of a 96 well plate was seeded with 2000 cells in 200 μl of each drug dilution in duplicate. A plate was stopped and fixed for each time point, stained with Giemsa and then read in a Titertek plate reader at 650 nm, and the absorbances were calibrated with known cell numbers on control plates. NHEK's were obtained from Clonetics Corporation at the secondary stage. Antiproliferative assays were done as for the murine keratinocytes. Media (KGM) without serum was supplied by Clonetics also. Normal Human Fibroblasts and MDBK cells were grown under the same conditions except that MDBK cells were grown at 41° C.

TABLE 5

Activities of Analogs of Compound A in Proliferation Assays vs PAPp26 Murine Keratinocytes and Normal Human Epidermal Keratinocytes

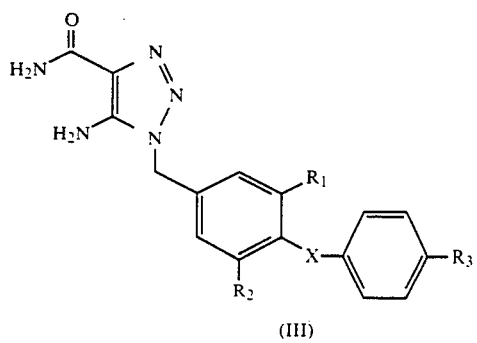

(III)

| Compound | $R_1$ | $R_2$ | X | $R_3$ | $ED_{50}$ PAPp26 mg/ml | $ED_{50}$ NHEK mg/ml |
|---|---|---|---|---|---|---|
| (B) | Cl | Cl | C=O | Cl | 2 | .5–1 |
| (C) | Cl | H | S | Cl | 1–2 | .5 |
| (D) | H | CF$_3$ | S | Cl | 1–2 | .5 |
| (E) | Cl | CH$_3$ | C=O | CF$_3$ | 2 | 1 |
| (F) | Cl | Cl | C=O | CN | 2 | 1 |
| (G) | Cl | Br | C=O | Cl | 2 | .5 |
| (H) | Cl | Cl | O | Br | 1–2 | .5 |
| (J) | Cl | Cl | C=O | Br | 1–2 | .5–1 |
| (K) | Cl | Cl | O | NO$_2$ | 2 | .5 |
| (L) | Cl | CH$_3$ | O | Cl | 2 | .5 |

TOPICAL ANTIPROLIFERATIVE ACTIVITY IN PIG SKIN

Compound A inhibits labelled thymidine incorporation into intact pig skin and also inhibits keratinocyte proliferation as measured by metaphase arrest with colchicine. The experiments described below demonstrate that the drug is active topically as an antiproliferative and that the effects are dependent upon vehicle.

In one experiment, a 20 kg pig was sedated and multiple areas of clipped skin were exposed to uv radiation sufficient to provoke a moderate hyperproliferative response within several days of exposure. On days 0, 1, 2 and 3 replicate irradiated sites were treated topically with Compound A in several vehicles or solvents. Topical preparations included a 2% drug in Gel #1, a combination of isopropyl myristate:Crodamol:ethanol, 1:1:2, or DMSO. The hyperproliferative response of the skin to uv was assessed on day 4 by injecting ³H-thymidine intradermally, and, 1 hour later, removing the sites by punch biopsy and processing the samples for autoradiography. Such autoradiographs indicate the number of epidermal cells in S phase synthesizing DNA and this is a common tool used by dermatologists to assess inhibition of proliferation in vivo. A single injection of methotrexate, 4 hours prior to ³H-thymidine injection was used as a positive control for inhibition of DNA synthesis. A labelling index, L.I., which is the percent of the total number of epidermal basal cells (keratinocytes) counted showing label incorporation. The results are shown in Table 6. Four days after exposure to uv, the L.I. of pig skin increased from 7.6% to 20.8% (normal human skin ca. 2%, psoriatic lesions ca. 25%, for comparison). Daily application of Compound A dramatically reduced the uv induced hyperproliferation in Gel #1, was less effective in Crodamol and, with this protocol, showed no effect with DMSO as the vehicle. The inhibition of proliferation by Compound A in Gel #1 was comparable to that for injected methotrexate.

TABLE 6

Effect of Compound A on UV Induced Hyperproliferation in Pig Skin In Vivo

| Treatment | Total Basal Cells Counted | Labelled Cells | LI % | % Inhibition |
|---|---|---|---|---|
| Normal, Gel #1 | 1057 | 81 | 7.6 | — |
| uv exposed, Gel #1 | 1496 | 312 | 20.8 | — |
| Compound A, DMSO | 744 | 150 | 20.1 | 0 |
| Compound A, Crodamol | 963 | 165 | 17.0 | 29 |
| Compound A, Gel #1 | 1020 | 57 | 5.6 | 100 |
| Methotrexate, i.d. | 1175 | 100 | 8.5 | 93 |

Compound A demonstrated significant in vivo activity in nude mice against P388 leukemia. The doses used were 240, 120 and 60 mg/kg delivered i.p. once per day for five days. The life prolongation assay with typical control survival times of 15 to 20 days gave values of 134%, 124% and 127% for the three drug concentrations. The length of survival time increase is similar to the length of time the animals were dosed.

The following example illustrates the preparation of the compounds useful in the method of treatment of the present invention, but does not limit the scope of the invention.

EXAMPLE

Preparation of 5-Amino-1-(4-[4-chlorobenzoyl]-3,5-dichlorobenzyl)-1,2,3-triazole-4-carboxamide Step A: Preparation of 3,5-dichlorobenzyl alcohol, 2

To a stirred solution of 3,5-dichlorobenzoyl chloride (712 mg, 3.40 mmole) in THF (6 ml) at 0° C. is added dropwise a solution of sodium borohydride (227 mg, 6.0 mmole), in N-methyl pyrrolidinone (1.5 ml) maintaining the temperature at ≦18° C. The reaction mixture is stirred for 2 hours at ambient temperature and then partitioned with 0.5N aqueous HCl (60 ml) and EtOAc (60 ml). The layers are separated and the aqueous layer is washed with EtOAc (20 ml). The combined organic layer is washed with H₂O (60 ml) and brine (40 ml), dried (Na₂SO₄), filtered, and concentrated to give crude product as a crystalline solid. One recrystallization from hot cyclohexane (7.5 ml) gives 2, i.e., 3,5-dichlorobenzyl alcohol (451 mg, 2.55 mmole, 75%, m.p. 77°–77.5° C.).

Step B: Preparation of 3,5-dichlorobenzyl t-butylsilylether, 3

In a 100-ml round-bottomed flask under nitrogen are dissolved alcohol 2 (4.80 g, 27.1 mmole), imidazole (4.60 g, 67.6 mmole) and a catalytic amount of 4-dimethylaminopyridine (16 mg, 0.13 mmole) in DMF (9 ml). t-Butyldimethylsilyl chloride (4.29 g, 28.5 mmole) is added (caution-exothermic) and the reaction mixture is stirred at ambient temperature for ca. 4 hours. The reaction is followed by reverse phase HPLC weight percent assay. Disappearance of starting material 2 is monitored by dissolving a known weight of the reaction mixture in 10 ml of eluant (the concentration should be ca. 16 mg of reaction mixture/10 ml eluant) and analyzing on a DuPont Zorbax ODS-C8 column isocratically eluted at ambient temperature at a flow rate 2 ml/min with mobile phase of 55% $H_2O$, 45% $CH_3CN$, and 0.1% $H_3PO_4$, monitored by UV detection at 230 nm. Retention time of alcohol 2 is 5.1 min. The reaction is considered complete when <3% of alcohol 2 remains. Upon completion the reaction mixture is partitioned between hexane (80 ml) and 1N aqueous HCl (100 ml). The organic layer is separated and washed with 1N aqueous HCl (80 ml) and water (3×100 ml), dried ($Na_2SO_4$), and filtered. 3,5-dichloro-benzyl-t-butyl silyl ether, 3, can be isolated by concentrating the hexane solution to an oil. Pure 3 (oil) is obtained by silica gel preparative TLC with 2% EtOAc in hexane as eluant. Assay of 3 is performed by normal phase isocratic HPLC at ambient temperature on DuPont Zorbax Sil eluted at 2 ml/min with hexane monitored by UV detection at 230 nm. Retention time of 3 is 6.4 min.

Step C: Preparation of 4-(4-chlorobenzoyl)-3,5-dichlorobenzyl-t-butylsilylether The hexane is turned over to THF for the subsequent metallation by adding anhydrous THF (100 ml), concentrating under reduced pressure to ca. 50 ml, and adding additional THF (100 ml) and concentrating ca. 70 ml. To a solution of crude silyl ether 3 (ca. 27 mmole) in THF (ca. 70 ml, solution KF ≦60 mg/ml) under nitrogen cooled to −75° C. is added dropwise a solution of nBuLi in hexane (11.0 ml of a 2.70M solution, 29.7 mmole) maintaining a temperature of ≦−60° C. After stirring for 30 minutes at ≦60° C., the reaction mixture is cooled to −75° C. and a solution of 4-chlorobenzoyl chloride (5.42 g, 31 mmole) in THF (5 ml) is added dropwise at ≦60° C. After stirring for 3 hours at −70° C. to −60° C., the reaction mixture is quenched by the addition of 2N aqueous HCl (2 ml). The approximate extent of conversion is assayed by disappearance of silyl ether 3 using the normal phase HPLC weight percent conditions described above. The typical observed conversion of 85–90%.

Step D: Preparation of 3,5 dichloro-4-(4-chlorobenzoyl)-benzylalcohol, 5

Concentrated aqueous HCl (25 ml) is added to the above reaction mixture, which is allowed to warm to room temperature and aged for 12 hours. The reaction is monitored by silica gel TLC eluted with 10% EtOAc in hexane ($R_f$ 5: 0.03). Upon completion the reaction mixture is partitioned between EtOAc (100 ml) and cold $H_2O$ (300 ml) and the layers are separated. The organic layer is washed with $H_2O$ (150 ml), 1N aqueous NaOH (2×150 ml, thoroughly to remove 4-chlorobenzoic acid), $H_2O$ (150 ml), and 0.1N aqueous HCl. The organic layer is dried ($Na_2SO_4$), filtered, and concentrated to give crude crystalline 3,5-dichloro-4-(4-chlorobenzoyl)-benzyl alcohol, 5 (9.97 g), 60 weight percent pure (70% assay yield from alcohol 2) by HPLC assay on DuPont Zorbax ODS-C8 eluted isocratically at ambient temperature at 2 ml/min with 55% $H_2O$, 45% $CH_3CN$, and 0.1% $H_3PO_4$ and monitored by UV detection at 230 mn (retention times, alcohol 2: 5.1 min; benzophenone 5: 14.4 min; 4-chlorobenzoic acid: 2.9 min).

Step E: Preparation of 3,5-dichloro-4(4-chlorobenzoyl)-benzylazide, 7

Sodium azide (6.2 g, 0.09 mole) was added to a stirred mixture of chloride 6 (22 g, of 66% pure 6, 14.5 g, 0.043 mole) and sodium iodide (1 g, 0.007 mole) in ethanol (150 ml). The mixture, under nitrogen, was heated at reflux for 3 hours and then allowed to cool to 20° C. The reaction mixture was poured into water and the product extracted into ether (200 ml, 2×100 ml). The combined organic phases were washed with water (3×100 ml), dried ($Na_2SO_4$) and evaporated under reduced pressure (<40° C.). The residue (23.7 g), a yellow-brown oil, was chromatographed on silica (150 g) eluted with 9:1 hexane:methylene chloride until pure azide 7 began to elute, then with 4:1 and 1:1 hexane:methylene chloride to complete the isolation of pure 7. Yield of 7 was 11.9 g (80%), mp 65°–68.5° C. The use of pure chloride 6 is expected to provide pure 7 without chromatography, although crystallization of 7 from hexane or hexane-ether may be required.

Step F: Preparation of 5-Amino-1-(4-[4-chlorobenzoyl]-3,5-dichlorobenzyl)-1,2,3-triazole-4-carboxamide Anhydrous milled potassium carbonate (119 g, 0.86 moles) ws suspended in DMSO (450 ml) for 10 minutes and the cyanoacetamide (18.2 g, 0.22 moles) was added. The slurry was stirred vigorously for 10 minutes, and then the solid azide (73.4 g, 0.22 moles) was added in one portion. After 16 hours, the mixture was filtered with suction and the solids rinsed with DMSO (500 ml). Water (4 L) was added to the combined extracts over 30 minutes with external cooling to maintain the temperature <30° C. The orange-yellow product was aged for 4 hours at 20° C. adn then filtered and washed with water (2 L). The filter cake was sucked dry and transferred to a 1 L flange flask containing ethyle acetate (500 ml). The mixture was heated under reflux with a Dean-Stark separator until no more water was collected. Ethyl acetate (200 ml) was removed by distillation and the red solution was allowed to cool and crystallize. The product was aged at 10° C. for 1 hour, filtered and washed with ethyl acetate (2×150 ml), dried at 50° C. in vacuo with an air bleed to provide 78.0 g yellow solid (85% yield, mp 202°–204° C.). Several batches (total weight 134.0 g) were combined and dissolved in methanol (5 L) at reflux temperature. The solution was filtered and concentrated to 1.8 L by distillation of methanol. The resulting slurry was cooled to 10° C., aged 1 hour, filtered and washed with methanol. The product was air dried, then further dried in vacuo at 40° C. to yield 122.5 g white crystalline solid (91% recovery; mp 202.0°–204° C.; HPLC: 210 nm and 254 nm single peak; DSC: 99.4 mol % at 2° C./min[MW=424.5]).

What is claimed is:

1. A method of treating a cancer susceptible to treatment with a compound of formula (I) in a patient with a surgically excised cancer tumor with a high probability of metastasis comprising: administration of a patient in need of such treatment a non-toxic therapeutically effective amount of compound of the following formula (I):

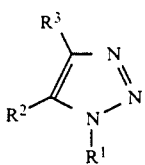

wherein:

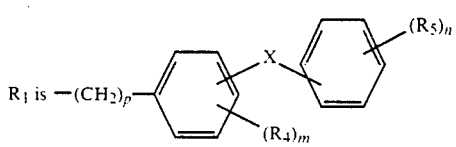

wherein
P is 0 to 2;
M is 0 to 4;
N is 0 to 5;
X is O, S, SO, $SO_2$, CO, CHCN, $CH_2$, or C=$NR_6$
where
$R_6$ represents
  (a) hydrogen;
  (b) loweralkyl;
  (c) hydroxy;
  (d) loweralkoxy;
  (e) amino;
  (f) loweralkylamino;
  (g) diloweralkylamino; or
  (h) cyano;
$R_4$ and $R_5$ independently are
  (a) halogen;
  (b) cyano;
  (c) trifluoromethyl;
  (d) loweralkanoyl;
  (e) nitro;
  (f) loweralkyl;
  (g) loweralkoxy;
  (h) carboxy;
  (i) carbalkoxy;
  (j) trifluoromethoxy;
  (k) acetamido;
  (l) loweralkylthio;
  (m) loweralkysulfonyl;
  (n) trichlorovinyl;
  (o) trifluoromethylthio;
  (p) trifluoromethylsulfinyl; or
  (q) trifluoromethylsulfonyl;
$R_2$ is
  (a) amino;
  (b) mono or diloweralkylamino;
  (c) acetamido;
  (d) acetimido;
  (e) ureido;
  (f) formamido;
  (g) formimido; or
  (h) quanidino; and
$R_3$ is
  (a) carbamoyl;
  (b) cyano;
  (c) carbazoyl;
  (d) amidino; or
  (e) N-hydroxycarbamoyl.

2. The method of claim 1 wherein n and m independently are 0, 1 or 2; P is 1; X is O, S, CO, or $CH_2$;
$R_4$ is
  (a) fluoro;
  (b) chloro;
  (c) bromo;
  (d) methyl;
  (e) trifluoromethyl;
  (f) cyano;
  (g) carbomethoxy;
  (h) trifluoromethoxy;
  (i) trifluoromethylthio;
  (j) nitro; or
  (k) trichlorovinyl;
$R_5$ is
  (a) chloro;
  (b) bromo;
  (c) fluoro;
  (d) methyl;
  (e) trifluoromethyl;
  (f) cyano;
  (g) carbalkoxy;
  (h) triclorovinyl; or
  (i) nitro.

3. The method of claim 1 wherein the compound is the formula

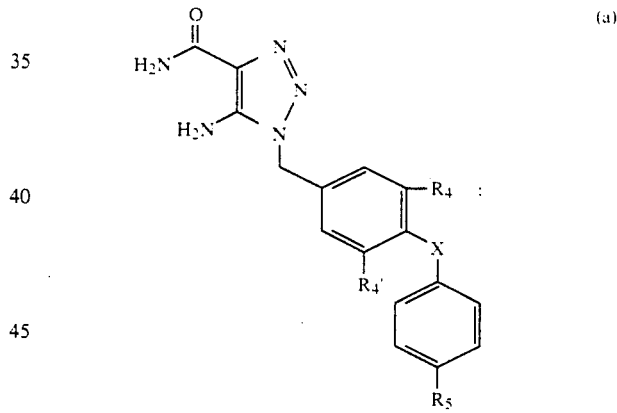

wherein X is $CH_2$, S, O, or CO; $R_4$ is Cl, $CF_3$, Br or $CH_3$; and $R_5$ is Cl, Br or $NO_2$.

4. A method of treatment of a cancer susceptible to treatment with a compound of formula (I), said cancer involving the transportion of individual cells to other tissues from a metastasizing tumor comprising:
   administration to a patient in need of such treatment an anti-proliferative, anti-metastatic effective amount of composition containing as its active ingredient the compound of the following formula (I):

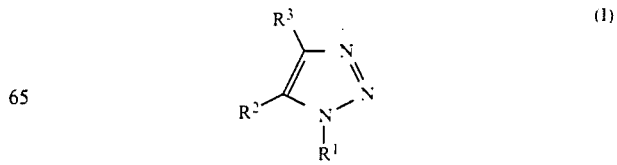

wherein:

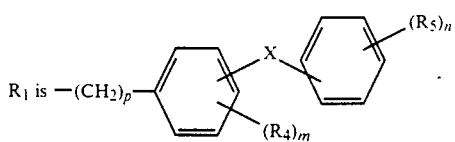

wherein P is 0 to 2;
M is 0 to 4;
N is 0 to 5;
X is O, S, SO, SO$_2$, CO, CHCN, CH$_2$ or C=NR$_6$
where
R$_6$ represents
(a) hydrogen;
(b) loweralkyl;
(c) hydroxy;
(d) loweralkoxy;
(e) amino;
(f) loweralkylamino;
(g) diloweralkylamino; or
(h) cyano;
R$_4$ and R$_5$ independently are
(a) halogen;
(b) cyano;
(c) trifluoromethyl;
(d) loweralkanoyl;
(e) nitro;
(f) loweralkyl;
(g) loweralkoxy;
(h) carboxy;
(i) carbalkoxy;
(j) trifluoromethoxy;
(k) acetamido;
(l) loweralkylthio;
(m) loweralkyslulfonyl;
(n) trichlorovinyl;
(o) trifluoromethylthio;
(p) trifluoromethoylsulfinyl; or
(q) trifluoromethylsulfonyl;
R$_2$ is
(a) amino;
(b) mono or diloweralkylamino;
(c) acetamido;
(d) acetimido;
(e) ureido;
(f) formamido;
(g) formimido; or
(h) quanidino; and
R$_3$ is (a) carbamoyl;
(a) cyano;
(b) carbazoyl;
(c) amidino; or
(d) N-hydroxycarbamoyl.

5. The method of claim 4 wherein n and m independently are 0, 1 or 2; P is 1; X is O, S, CO, or CH$_2$;
R$_4$ is
(a) fluoro;
(b) chloro;
(c) bromo;
(d) methyl;
(e) trifluoromethyl;
(f) cyano;
(g) carbomethoxy;
(h) trifluoromethoxy;
(i) trifluoromethylthio;
(j) nitro; or
(k) trichlorovinyl;
R$_5$ is
(a) chloro;
(b) bromo;
(c) fluoro;
(d) methyl;
(e) trifluoromethyl;
(f) cyano;
(g) carbalkoxy;
(h) trichlorovinyl; or
(i) nitro.

6. The method of claim 4 wherein the compound is the formula

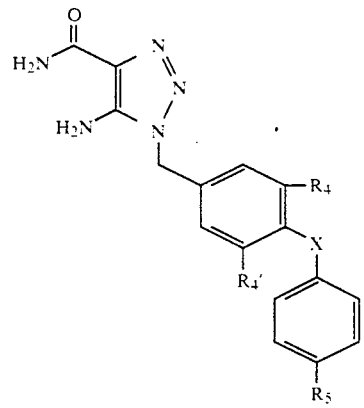

wherein X is CH$_2$, SO, O, or CO; R$_4$ is Cl, CF$_3$, Br or CH$_3$; and R$_5$ is Cl, Br or NO$_2$.

7. A method of treating a cancer susceptible to treatment with a compound which is 5-amino-1-(4-[4-chlorobenzoyl]-3,5-dichlorobenzyl)-1,2,3-triazole-4-carboxamide, said cancer in a patient with a surgically excised cancer tumor with a high probability of metastasis comprising:
administration to a patient in need of such treatment a non-toxic therapeutically effective amount of compound which is 5-amino-1-(4-[4-chlorobenzoyl]-3,5-dichlorobenzyl)-1,2,3-triazole-4-carboxamide.

8. A method of treatment of a cancer susceptible to treatment with a compound which is 5-amino-1-(4-[4-chlorobenzoyl]-3,5-dichlorobenzyl)-1,2,3-triazole-4-carboxamide, said cancer involving the transportation of individual cells to other tissues from a metastasizing tumor comprising:
administration to a patient in need of such treatment an anti-proliferative, anti-metastatic effective amount of composition containing as its active ingredient the compound which is 5-amino-1-(4-[4-chlorobenzoyl]-3,5-dichlorobenzyl)-1,2,3-triazole-4-carboxamide.

* * * * *